United States Patent
Kourai et al.

(10) Patent No.: US 7,612,097 B2
(45) Date of Patent: Nov. 3, 2009

(54) METHOD FOR PRODUCING BACTERICIDAL PYRIDINE COMPOUND AND BACTERICIDAL PYRIDINE COMPOUND

(75) Inventors: Hiroki Kourai, 230-2, Tomiyoshi, Kawauchi-cho, Tokushima-shi, Tokushima (JP) 771-0112; Yoshio Igarashi, Yashio (JP); Hirobumi Nobeshima, Yashio (JP); Satoshi Metoki, Yashio (JP)

(73) Assignees: Tama Kagaku Kogyo Co., Ltd., Yashio-shi (JP); Hiroki Kourai, Tokushima-shi (JP)

( * ) Notice: Subject to any disclaimer, the term of this patent is extended or adjusted under 35 U.S.C. 154(b) by 564 days.

(21) Appl. No.: 10/578,870

(22) PCT Filed: Nov. 8, 2004

(86) PCT No.: PCT/JP2004/016540

§ 371 (c)(1),
(2), (4) Date: May 11, 2006

(87) PCT Pub. No.: WO2005/044800

PCT Pub. Date: May 19, 2005

(65) Prior Publication Data

US 2007/0099961 A1    May 3, 2007

(30) Foreign Application Priority Data

Nov. 11, 2003  (JP) .............................. 2003-380664
May 12, 2004   (JP) .............................. 2004-142749
Jun. 18, 2004  (JP) .............................. 2004-180648

(51) Int. Cl.
  *C07D 401/02*  (2006.01)
  *A61K 31/444* (2006.01)
(52) U.S. Cl. ...................................... 514/332; 546/266
(58) Field of Classification Search ........................ None
  See application file for complete search history.

(56) References Cited

FOREIGN PATENT DOCUMENTS

| | | |
|---|---|---|
| JP | 6-321902 | 11/1994 |
| JP | 7-191438 | 7/1995 |
| JP | 8-301703 | 11/1996 |
| JP | 10-95773 | 4/1998 |
| JP | 2000-159608 | 6/2000 |
| JP | 2003-146956 | 5/2003 |
| JP | 2003-267953 | 9/2003 |
| WO | 2004/063160 | 7/2004 |

*Primary Examiner*—Zinna N Davis
(74) *Attorney, Agent, or Firm*—Oblon, Spivak, McClelland, Maier & Neustadt, L.L.P.

(57) ABSTRACT

Provided are novel pyridine compounds represented by the following formula (7):

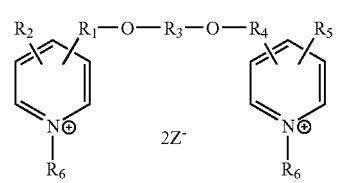

Formula (7)

wherein $R_1$ and $R_4$ may be the same or different and are each a linear or branched alkyl group having 1 to 4 carbon atoms; $R_2$ and $R_5$ are hydrogen atoms, or may be the same or different and are each a halogen atom, lower alkyl group or lower alkoxy group; $R_3$ is a linear or branched alkyl group having 2 to 12 carbon atoms; $R_6$ is a linear or branched alkyl group having 1 to 18 carbon atoms; and Z is a chlorine atom, bromine atom or iodine atom or an $OSO_2R_7$ group in which $R_7$ is a lower alkyl group or a substituted or unsubstituted phenyl group. Also provided is their production process, which can easily provide them at low cost from readily-available pyridine compounds as starting raw materials.

2 Claims, No Drawings

METHOD FOR PRODUCING BACTERICIDAL PYRIDINE COMPOUND AND BACTERICIDAL PYRIDINE COMPOUND

This application is a 371 of PCT/JP04/16540 filed Nov. 8, 2004.

TECHNICAL FIELD

This invention relates to novel pyridine compounds having microbicidal activities and a process for their industrial production.

BACKGROUND ART

Bis-quaternary ammonium compounds which exhibit antimicrobial activities against bacteria, fungi and the like are known for many years, and are still used widely as antimicrobial agents at present. The currently-employed, antimicrobial bis-quaternary ammonium compounds are generally excellent in antimicrobial activities, but at the same time, biodegradation products of these compounds have high residual toxicity. Concerning the actual use of these compounds, they involve problems in the safety to the environment and the solubility and safety to water so that a limitation is imposed on the applicable range thereof. Further, the conventional bis-quaternary ammonium compounds are also accompanied by drawbacks in that their antimicrobial power is competed with saccharides, proteins, lipids and the like; their antimicrobial power is lowered in a low pH (acidic) range, and they are not effective against microbial endospores.

Accordingly, there have been reported bis-quaternary ammonium compounds represented by the following formula (A) or (B) (Patent Document 1):

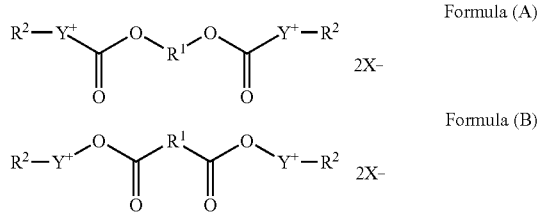

wherein Y represents a substituted or unsubstituted pyridine ring, quinoline ring, isoquinoline ring or thiazoline ring, $R^1$ represents a substituted or unsubstituted alkylene group or alkenylene group having 2 to 10 carbon atoms, $R^2$ represents a substituted or unsubstituted alkyl group having 6 to 18 carbon atoms and bonded to the nitrogen atom of Y, and X represents an anion;

bis-quaternary ammonium compounds represented by the following formula (C) (Patent Document 2):

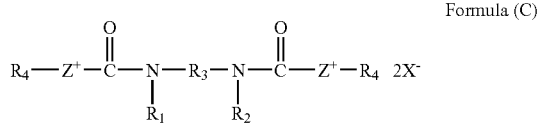

wherein Z represents a pyridine ring, $R_1$ and $R_2$ may be the same or different and each represents a hydrogen atom or an alkyl group having 1 to 6 carbon atoms, $R_3$ represents an alkenylene group having 3 to 18 carbon atoms, $R_4$ represents an alkyl or alkenyl group having 6 to 18 carbon atoms and bonded to the ring nitrogen atom of Z, and X represents an anion; and bis-quaternary ammonium compounds represented by the following formula (D) (Patent Document 3):

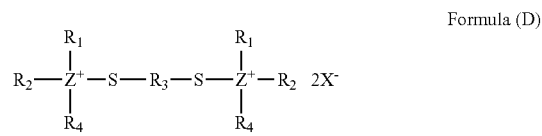

wherein Z represents a substituted or unsubstituted pyridine ring or quinoline ring, $R_3$ represents a substituted or unsubstituted alkylene or alkenylene group having 2 to 18 carbon atoms, $R_4$ represents a substituted or unsubstituted alkyl group having 6 to 18 carbon atoms and bonded to the nitrogen atom of Z, $R_1$ and $R_2$ may be the same or different and each represents an alkyl group having 1 to 3 carbon atoms, hydroxyl group, amino group, alkoxy group having 1 to 3 carbon atoms or hydrogen atom bonded to an atom in Z other than said nitrogen atom, and X represents an anion.

Patent Document 1: JP-A-8-301703
Patent Document 2: JP-A-10-095773
Patent Document 3: JP-A-6-321902

DISCLOSURE OF THE INVENTION

There is, accordingly, a strong demand for the development of bis-quaternary ammonium compounds, which are far better in antimicrobial activities than the above-described, conventionally-known bis-quaternary ammonium compounds, form biodegradation compounds having low residual toxicity, and are friendly to the global environment.

An object of the present invention is, therefore, to easily provide a novel microbicidal compound at low cost from a readily-available pyridine compound as a starting raw material.

The present invention provides a microbicidal pyridine compound represented by the following formula (7):

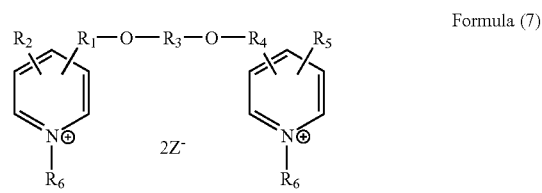

wherein $R_1$ and $R_4$ may be the same or different and are each a linear or branched alkyl group having 1 to 4 carbon atoms; $R_2$ and $R_5$ are hydrogen atoms, or may be the same or different and are each a halogen atom, lower alkyl group or lower alkoxy group; $R_3$ is a linear or branched alkyl group having 2 to 12 carbon atoms; $R_6$ is a linear or branched alkyl group having 1 to 18 carbon atoms, especially preferably 8, 10 or 12 carbon atoms; and Z is a chlorine atom, bromine atom or iodine atom or an $OSO_2R_7$ group in which $R_7$ is a lower alkyl group or a substituted or unsubstituted phenyl group; and a process for its production. The compound is useful as an antimicrobial compound.

When producing the above-described compound, the process can be divided roughly into the following two steps. In the following description, $R_1$ to $R_7$ and Z have the same meanings as described above; the definitions of $R_1$ to $R_7$ and Z will be omitted in the description to be made hereinafter.

Described specifically,

1) Synthesis of a pyridine compound represented by the following formula (5):

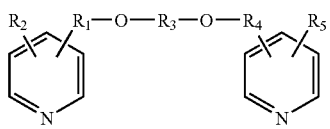

Formula (5)

2) Synthesis of the microbicidal pyridine compound of the formula (1) by a reaction between the compound of the formula (5) and a halogen compound or sulfonate ester compound represented by the following formula (6):

$$R_6\text{-}Z \qquad \text{Formula (6)}$$

The present inventors firstly mapped out the following plan as to a process for the synthesis of the novel pyridine compound represented by the formula (5). Namely, this process comprises the formation of an ether bond by a nucleophilic displacement reaction between a pyridine compound represented by the following formula (1):

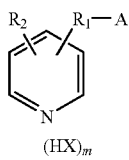

Formula (1)

wherein A is a group capable of functioning as a leaving group under an action of a base to make it possible to form an alkyl cation; $R_1$ and $R_2$ are as defined above; X is a counter anion for an inorganic or organic protonic acid; and m stands for 0 or 1, (m=0) or a salt (m=1) thereof, and a diol represented by the following formula (2):

$$HO\text{—}R_3\text{—}OH \qquad \text{Formula (2)}$$

In this case, the diol is needed to be activated by forming an alkoxide with a base. When the salt of the formula (1) is used, the base is needed further in an amount sufficient to also neutralize the salt.

Following the above-described plan, the present inventors proceeded with extensive research with primary objects directed to:

1) Selection of substituents capable of functioning as leaving groups.
2) Selection of bases enabling their elimination.
3) Selection of solvent species enabling their elimination.
4) Selection of highly-selective reaction conditions.

As a result, the present inventors found an efficient process for the production of a pyridine compound represented by the following formula (3):

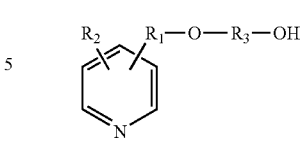

Formula (3)

Concerning the formation of a second ether bond by a nucleophilic displacement reaction between the pyridine compound represented by the formula (3) and a pyridine compound represented by the following formula (4):

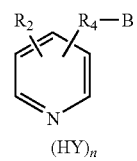

Formula (4)

wherein B is a substituent capable of functioning as a leaving group under an action of a base to make it possible to form an alkyl cation; Y is a counter anion for an inorganic or organic protonic acid; $R_4$ and $R_5$ are as defined above; B may be the same as or different from A defined above; Y may be the same as or different from X defined above; $R_4$ may be the same as or different from $R_1$ defined above; $R_5$ may be the same as or different from $R_2$ defined above; n stands for 0 or 1 and may be the same as or different from m defined above, (n=0) or a salt (n=1) thereof, the present inventors then proceeded with an extensive investigation by paying an attention to:

1) Selection of substituents capable of functioning as leaving groups.
2) Selection of bases enabling their elimination.
3) Selection of solvent species enabling their elimination.
4) Selection of highly-selective reaction conditions.

In the above reaction, the pyridine compound represented by the formula (3) needs to be activated by the formation of an alkoxide with a base. When the salt of the formula (4) is used, the base is needed in an amount sufficient to also neutralize the salt. As a result of conducting the investigation in various ways, the present inventors have found an efficient process for the production of the pyridine compound represented by the formula (5), leading to the completion of the present invention. It is to be noted that the definitions of A, B, X, Y, m and n will be omitted in the following description as they have the same meanings as defined above.

Finally, the present inventors also conducted an extensive investigation about desired conditions for the synthesis of the microbicidal pyridine compound represented by the formula (7) by the reaction between the pyridine compound represented by the formula (5) and the alkyl halide or sulfonate ester represented by the formula (6), resulting in the completion of the present invention. Described specifically, the present invention provides a novel microbicidal pyridine compound represented by the following formula (7):

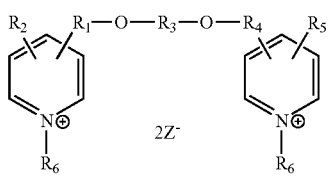

Formula (7)

by reacting a pyridine compound represented by the following formula (1):

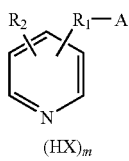

Formula (1)

and a diol represented by the following formula (2):

HO—R$_3$—OH      Formula (2)

in the presence of a strong base to produce a pyridine compound represented by the following formula (3):

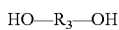

Formula (3)

reacting the compound and a pyridine compound represented by the following formula (4):

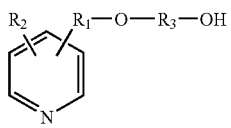

Formula (4)

in the presence of a strong base to produce a pyridine compound represented by the following formula (5):

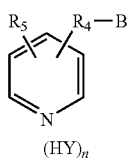

Formula (5)

reacting the compound and a halogen compound or sulfonate ester compound represented by the following formula (6):

R$_6$-Z      Formula (6)

and a production process thereof.

Among compounds encompassed by the formula (7), particularly-effective microbicidal compounds are compounds represented by the following formula (8), formula (9) or formula (10):

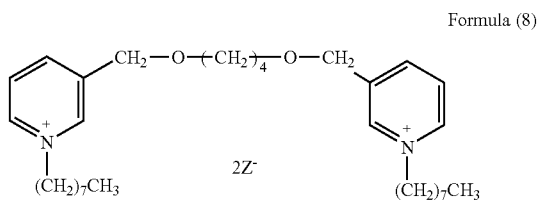

Formula (8)

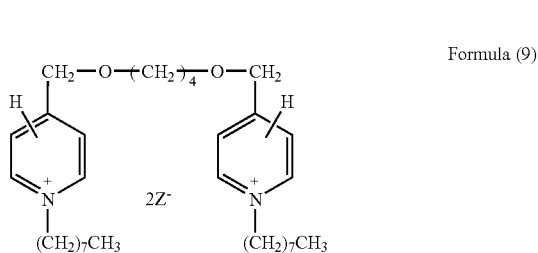

Formula (9)

wherein Z is a chlorine atom, bromine atom or iodine atom or an OSO$_2$R$_1$ group in which R$_1$ is a lower alkyl group or a substituted or unsubstituted phenyl group; or

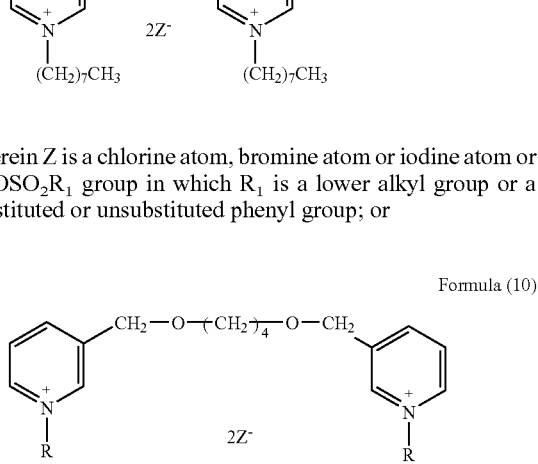

Formula (10)

wherein R is a —(CH$_2$)$_9$CH$_3$ group or a —(CH$_2$)$_{11}$CH$_3$ group, Z is a chlorine atom, bromine atom or iodine atom or an OSO$_2$R$_1$ group in which R$_1$ is a lower alkyl group or a substituted or unsubstituted phenyl group.

ADVANTAGEOUS EFFECT OF THE INVENTION

According to the present invention, novel microbicidal pyridine compounds can be easily provided at low cost from readily-available pyridine compounds as starting raw materials.

BEST MODES FOR CARRYING OUT THE INVENTION

The present invention will next be described in further detail based on certain preferred embodiments.

In the pyridine compound represented by the formula (1), the substituent represented by A and capable of functioning as a leaving group under an action of a base to make it possible to form a carbocation can be a chlorine atom, bromine atom, iodine atom, (lower alkyl)sulfonyloxy group, substituted or unsubstituted benzenesulfonyloxy group, or the like. The (lower alkyl)sulfonyloxy group can be a methanesulfonyloxy group, ethanesulfonyloxy group, or the like, and the substituted or unsubstituted benzenesulfonyloxy group can be a benzenesulfonyloxy group, 4-methylbenzenesulfonyloxy group, 4-methoxybenzenesulfonyloxy group, 4-chlorobenzenesulfonyloxy group, or the like. As the substituent A, a chlorine atom is particularly preferred.

In the formula (1), the linear or branched alkyl group having 1 to 4 carbon atoms and represented by $R_1$ can be a —$CH_2$— group, —$(CH_2)_2$— group, —$(CH_2)_3$— group, —$(CH_2)_4$— group, —$CH_3CH$— group, —$(CH_3)_2C$— group, —$(CH_3CH_2)C(CH_3)$— group, or the like. Particularly preferred is a —$CH_2$— group. $R_2$ can be a hydrogen atom, fluorine atom, chlorine atom, bromine atom, iodine atom, methyl group, ethyl group, propyl group, butyl group, isopropyl group, isobutyl group, tertiarybutyl group, methoxy group, ethoxy group, propoxy group, butoxy group, or the like. Particularly preferably, R, is a —$CH_2$— group and $R_2$ is a hydrogen atom, although no particular limitations are imposed on the positions of substitution by the substituents $R_1$ and $R_2$.

In the formula (1), X can be a chlorine anion, bromine anion, iodine anion, lower alkylsulfonyloxy anion, substituted or unsubstituted benzenesulfonyloxy anion, (lower alkyl)carboxy anion, substituted or unsubstituted, benzenecarboxy anion, or the like. Particularly preferred X is a chlorine anion. Further, the lower alkylsulfonyloxy anion can be a methanesulfonyloxy anion, ethanesulfonyloxy anion, or the like, the substituted or unsubstituted benzenesulfonyloxy anion can be a benzenesulfonyloxy anion, 4-methylbenzenesulfonyloxy anion, 4-methoxybenzenesulfonyloxy anion, 4-chlorobenzenesulfonyloxy anion, or the like. On the other hand, the (lower alkyl)carboxy anion can be an acetoxy anion, propionyloxy anion, or the like, and the substituted or unsubstituted benzenecarboxy anion can be a benzoyloxy anion, 4-methylbenzoyloxy anion, 4-methoxybenzoyloxy anion, 4-chlorobenzoyloxy anion, or the like.

When m=0 in the formula (1), the compound of the formula (1) is a free pyridine base. When m=1 in the formula (1), on the other hand, the compound of the formula (1) is any desired one of its corresponding various inorganic acid or organic acid salts.

The starting raw material, i.e., the pyridine compound represented by the formula (1) can be obtained by various processes. Usable examples include free bases such as 2-chloromethylpyridine, 3-chloromethylpyridine and 4-chloromethylpyridine, and their salts; free bases such as 2-bromomethylpyridine, 3-bromomethylpyridine and 4-bromomethylpyridine, and their salts; free bases such as 2-iodomethylpyridine, 3-iodomethylpyridine and 4-iodomethylpyridine, and their salts; free bases such as 2-(methanesulfonyloxy)methylpyridine, 3-(methanesulfonyloxy)methylpyridine and 4-(methanesulfonyloxy)methylpyridine, and their salts; and free bases such as 2-(benzenesulfonyloxy)methylpyridine, 3-(benzenesulfonyloxy)methylpyridine and 4-(benzenesulfonyloxy)methylpyridine, and their salts. Particularly preferred are 3-chloromethylpyridine and 4-chloromethylpyridine.

In the formula (2), the diol which contains as $R_3$ a linear or branched alkyl group having 2 to 12 carbon atoms can be obtained by various processes, and can be used in the present invention. Usable examples include diols such as ethylene glycol, propylene glycol, 1,2-propanediol, 1,4-butanediol, 1,2-butanediol, 2,3-butanediol, 1,5-pentanediol, 1,6-hexanediol, 1,8-octanediol, 1,10-decanediol, 2-methyl-2,4-pentanediol, and 2-ethyl-1,3-hexanediol; diols containing one or more unsaturated bonds, such as 2-butene-1,4-diol; and diols containing one or more ether bonds, such as diethylene glycol and triethylene glycol. Particularly preferred is 1,4-butanediol.

The pyridine compound or its salt represented by the formula (1) may be used preferably in an amount of from 1 equivalent mole to 1.5 equivalent moles, more preferably in an amount of from 1 equivalent mole to 1.1 equivalent moles per mole of the diol represented by the formula (2).

Upon production of the pyridine compound of the formula (3) by the reaction between the pyridine compound represented by the formula (1) and the diol represented by the formula (2), various reaction conditions can be used. The presence of a strong base is essential for conducting the reaction, because it is important for forming a corresponding alkoxide from the diol represented by the formula (2) to form a corresponding alkoxide. Strong bases usable in this reaction include metal lithium, metal potassium, metal sodium, and hydrides thereof; the hydroxides of metal lithium, metal potassium and metal sodium; alkyl lithiums such as methyl lithium and butyl lithium; phenyl lithium; and alkali metal tertiary alkoxides such as lithium tertiary butoxide, potassium tertiary butoxide and sodium tertiary butoxide. From economy, safety and convenience, sodium tertiary butoxide and potassium tertiary butoxide are suited. When the hydroxide of an alkali metal is employed as a strong base, the use of a phase transfer catalyst such as a quaternary ammonium salt is preferred because the velocity of the reaction between the pyridine compound and the diol can be accelerated. These strong bases can be used either singly or in combination.

When the free base of the pyridine compound represented by the formula (1) is employed as a raw material in this reaction, the strong base may be used in an amount of about 1 equivalent mole. When the pyridine compound represented by the formula (1) is in the form of a salt, the strong base may be used in an amount of about 2 equivalent moles as a sum of about 1 equivalent mole needed to neutralize the salt and about 1 equivalent mole to be consumed in the desired reaction. If the conversion is low, however, the strong base may be added further until the pyridine compound represented by the formula (1) is used up. The strong base to be used upon neutralizing the salt and the strong base to be used in the desired reaction may be the same or different. As the pyridine compound represented by the formula (1) is prone to a modification by its contact with the strong base, it is preferred to form an alkoxide beforehand by the reaction between the diol represented by the formula (2) and the strong base and then to react the alkoxide with the pyridine compound represented by the formula (1); or to mix the pyridine compound represented by the formula (1) and the diol represented by the formula (2) together in advance and then to add the strong base into the resultant mixture. When the pyridine compound represented by the formula (1) is in the form of a salt, it is possible to add beforehand the strong base in an amount sufficient to convert the compound into its free form and then to perform the treatments by the above-mentioned procedure.

This reaction can be conducted generally in the presence of any desired one of various solvents. As a solvent capable of achieving a good conversion and selectivity in the desired reaction without adversely affecting the desired reaction, it is preferred to use an aprotonic polar solvent. As the aprotonic polar solvent, a cyclic ether solvent such as tetrahydrofuran or dioxane, an amide solvent such as dimethylformamide, N-methylpyrrolidone or dimethylimidazolidinone, or the like can be used suitably. Taking the economy and the ease in post treatments into consideration, dimethylformamide is the most suitable solvent. These solvents can be used either singly or in combination. The solvent can be used in an amount suitably determined in view of the solubility of the pyridine compound or its salt represented by the formula (1), the solubility of the diol represented by the formula (2), said pyridine compound or its salt and said diol being raw materials, and the state of dispersion of the alkali metal salt to be formed in the course of the reaction.

The temperature of the reaction can be chosen from −20° C. to the boiling point under normal pressure of the solvent to be used. The preferred reaction temperature may be from −20° C. to room temperature, and the more preferred reaction temperature may be from −10° C. to 10° C. The progress of the reaction can be monitored by thin-layer chromatography or high-performance liquid chromatography, and the end of the reaction can be confirmed based on the full consumption of the raw materials.

The pyridine compound represented by the formula (3), which has been obtained by this reaction, can be collected from the reaction mixture in a manner known per se in the art. For example, the reaction mixture after the completion of the reaction is subjected to solid-liquid separation to remove the resultant alkali metal salt. After the mother liquor is concentrated under reduced pressure, the liquid residue is dispersed in water, followed by extraction. The extract is then concentrated under reduced pressure. The compound can be obtained with still higher purity by forming an inorganic or organic acid salt of the pyridine compound represented by the formula (3) such as its hydrochloride, acetate or sulfate, optionally conducting its recrystallization as needed, neutralizing the salt, and then conducting post-treatments by methods known per se in the art.

The pyridine compound represented by the formula (5) can next be obtained by reacting the pyridine compound represented by the formula (3) with the pyridine compound or its salt represented by the formula (4) in the presence of the strong base.

As the pyridine compound or its salt represented by the formula (4), a compound similar to the pyridine compound or its salt represented by the formula (1) can be chosen. In this case, when $R_1 \neq R_4$ or $R_2 \neq R_5$ in the pyridine compound or its salt represented by the formula (4) and the pyridine compound or its salt represented by the formula (1), the resulting pyridine compound represented by the formula (5) will be a compound which contains different pyridylalkyl groups or different substituents on the two pyridine rings. When $R_1=R_4$ and $R_2=R_5$, on the other hand, the resulting pyridine compound represented by the formula (5) will be a compound which contains the same pyridylalkyl groups or the same substituents on the two pyridine rings.

When the diol represented by the formula (2) to be used in the production of the pyridine compound represented by the formula (3) is a symmetrical diol and further, when $R_1=R_4$ and $R_2=R_5$ in the pyridine compound or its salt represented by the formula(4) and the pyridine compound or its salt represented by the formula (1), the resulting pyridine compound represented by the formula (5) will be a compound having a bilaterally symmetrical structure.

The pyridine compound represented by the formula (5) can be produced without isolation of the compound represented by the formula (3). For example, the pyridine compound represented by the formula (3) may be formed in a reaction system by such a procedure as mentioned above, and the pyridine compound represented by the formula (4) may then be reacted in the presence of the strong base. This procedure is effective when $R_1=R_4$ and $R_2=R_5$ in the pyridine compounds or their salts represented by the formulae (4) and (1), and extremely effective when A=B and X=Y further in the pyridine compounds or their salts represented by the formulae (4) and (1).

The pyridine compound or its salt represented by the formula (4) may be used preferably in an amount of from 1 to 1.5 equivalents, more preferably in an amount of from 1 to 1.1 equivalents to the pyridine compound represented by the formula (3).

In the reaction between the pyridine compound represented by the formula (3) and the pyridine compound or its salt represented by the formula (4), the pyridine compound or its salt represented by the formula (4) is prone to a modification by its contact with the strong base as mentioned above. It is, therefore, preferred to form an alkoxide of the compound of the formula (3) beforehand by the reaction between the pyridine compound represented by the formula (3) and the strong base and then to add the pyridine compound represented by the formula (4); or to mix the pyridine compound represented by the formula (3) and the pyridine compound represented by the formula (4) together in advance and then to add the strong base. When the pyridine compound represented by the formula (4) is in the form of a salt, it is possible to add beforehand the strong base in an amount sufficient to convert the compound into its free form, generally in an amount of about 1 equivalent mole and then to conduct treatments by the above-mentioned procedure.

In this reaction, specifically in the reaction between the pyridine compound or its salt represented by the formula (1) and the diol represented by the formula (2), desired one or more of selected strong bases can be used. These strong bases can, therefore, be used either singly or in combination. When the pyridine compound represented by the formula (4) is a free base, the strong base may be used preferably in an amount of about 1 equivalent mole per mole of the pyridine compound represented by the formula (4). If the conversion is low, however, the strong base may be added further until the pyridine compound represented by the formula (3) and the pyridine compound represented by the formula (4) are used up.

In this reaction, specifically in the reaction between the pyridine compound or its salt represented by the formula (1) and the diol represented by the formula (2), desired one or more of selected solvents can be used. These solvents can, therefore, be used either singly or in combination. The solvent can be used in an amount suitably determined in view of the solubilities of the pyridine compound or its salt represented by the formula (3) and the pyridine compound or its salt represented by the formula (4) and the state of dispersion of the alkali metal salt to be formed in the course of the reaction.

This reaction can choose from −20° C. to the boiling point under normal pressure of the solvent to be used. The preferred reaction temperature may be from −20° C. to room temperature, and the more preferred reaction temperature may be from −10° C. to 10° C. The progress of the reaction can be monitored by thin-layer chromatography or high-performance liquid chromatography, and the end of the reaction can be confirmed based on the full consumption of the raw materials. The pyridine compound represented by the formula (5) can be collected from the reaction mixture in a manner known per se in the art. When the compound is crystalline, the compound can be obtained with still higher purity by conducting recrystallization. When the compound is amorphous, on the other hand, the compound can be obtained with high purity by forming an inorganic or organic acid salt of the compound such as its monohydrochloride, dihydrochloride, monoacetate or diacetate, optionally conducting its recrystallization as needed, neutralizing the salt, and then collecting the resultant product in a manner known per se in the art.

The desired microbicidal pyridine compound represented by the formula (7) can then be obtained by reacting the pyridine compound represented by the formula (5) with the halogen compound or sulfonate ester compound represented by the formula (6). In the formula (6), a linear or branched alkyl group having 1 to 18 carbon atoms, especially preferably 8, 10 or 12 carbon atoms can be selected as $R_6$, and a halogen atom such as a chlorine atom, bromine atom or iodine atom or a substituted sulfonyloxy group represented by an $OSO_2R_7$ group can be selected as Z. In this case, a lower alkyl group or a substituted or unsubstituted phenyl group can be selected as $R_7$. Examples of the halogen compound represented by the formula (6) include alkyl chlorides, alkyl bromides, alkyl iodides and the like, each of which contains 1 to 18 carbon atoms, especially preferably 8, 10 or 12 carbon atoms. Examples of the sulfonate ester, on the other hand, include lower alkyl sulfonate esters of aliphatic alcohols having 1 to 18 carbon atoms, especially preferably 8, 10 or 12 carbon atoms and substituted or unsubstituted benzenesulfonate esters.

In this reaction, the halogen compound or sulfonate ester compound represented by the formula (6) can be used theoretically in an amount of 2 equivalent moles per mole of the pyridine compound represented by the formula (5). If the conversion is low, however, the compound of the formula (6) may be used in a still greater amount. When used in large excess, it can be recovered and reused.

A solvent can be used in the reaction between the pyridine compound represented by the formula (5) and the halogen compound or sulfonate ester compound represented by the formula (6). As a preferred solvent, a lower aliphatic alcohol or an aprotonic polar solvents can be mentioned. Specifically, methanol, ethanol, propanol, isopropanol, butanol, isobutanol, tertiary butanol, acetonitrile, propionitrile, acetone, methyl ethyl ketone, methyl isobutyl ketone, tetrahydrofuran, dioxane, dimethylformamide, N-methylpyrrolidone, dimethylimidazolidinone, dimethylsulfoxide or the like can be used. Dimethylformamide is the most preferred solvent for good conversion and selectivity of the reaction, easy post-treatment and excellent economy.

These solvents can be used either singly or in combination. The solvents can be used in an amount suitably determined in view of the solubilities of the pyridine compound represented by the formula (5) and the halogen compound or sulfonate ester compound represented by the formula (6).

As an alternative, the reaction can also be conducted by using the halogen compound or sulfonate ester compound, which is represented by the formula (6), to excess instead of using any solvent. This method is extremely efficient and economical, because subsequent to the completion of the reaction, the unreacted compound represented by the formula (6) can be separated and recovered from the reaction mixture for its reuse.

This reaction can be conducted at from 20° C. to the boiling point under normal pressure of the solvent to be used or the compound represented by the formula (6). The preferred temperature may be from room temperature to 100° C., and the more preferred temperature may be from 40° C. to 80° C. The progress of the reaction can be monitored by high-performance liquid chromatography or the like, and the end of the reaction can be determined based on the full consumption of the raw materials and the produced amount of the microbicidal pyridine compound of the formula (7) as the target.

It is also possible to continuously conduct the reaction by adding the compound represented by the formula (6) to the reaction mixture, which contains the pyridine compound represented by the formula (5), without isolating the pyridine compound represented by the formula (5). In this case, the solvent employed in the production of the compound of the formula (5) can be used as is.

The microbicidal pyridine compound represented by the formula (7) can be collected in a manner known per se in the art. When the compound is solid at room temperature, it can be crystallized from a suitable solvent system. In this case, the selection of a suitable solvent system makes it possible to effect purification by recrystallization and hence to obtain the target product with high purity.

EXAMPLES

The present invention will be described in further detail based on the following Examples.

Example 1

Synthesis of a Compound (3-A) Represented by the following Structural Formula

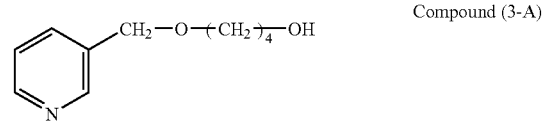

Compound (3-A)

1,4-Butanediol (8.24 g, 91.43 mmol) was added to DMF (dimethylformamide) (75 mL), and under ice cooling, potassium tert-butoxide (10.3 g, 91.79 mmol) was added, followed by stirring at room temperature for 1.5 hours.

To the resultant slurry, 3-chloromethylpyridine hydrochloride (1.0 g, 6.10 mmol) and potassium tert-butoxide (0.68 g, 6.06 mmol) were consecutively added at −8 to −3° C. That procedure was repeated 15 times, so that 3-chloromethylpyridine hydrochloride (15.0 g, 91.45 mmol) and potassium tert-butoxide (10.2 g, 90.9 mmol) were added in total.

After completion of the addition, the reaction mixture was analyzed by HPLC (under Conditions 1). As the peak of 3-chloromethylpyridine was confirmed, potassium tert-butoxide was added at below 5° C. until the peak of 3-chloromethylpyridine disappeared. The amount of the additional potassium tert-butoxide was 1.13 g (10.07 mmol).

The reaction mixture was subjected to solid-liquid separation, the resulting filter cake was washed with DMF (30 mL), and DMF was distilled off from the filtrate and washing under reduced pressure to obtain a crude product in the form of an oil (the compound (3-A)) (17.1 g). As a result of an analysis of the thus-obtained oil by HPLC (under Conditions 1), the area % of the compound (3-A) was determined to be 76.0%.

The crude product of the compound (3-A) was dissolved in water (30 mL), and was then washed with toluene. Subsequently, sodium chloride (6 g) was added to the water layer, followed by extraction with dichloromethane (20 mL×2). The extracts were dried over anhydrous magnesium sulfate, and the solvent was then distilled off to obtain the compound (3-A) in the form of an oil (9.21 g, yield: 57.2% based on 1,4-butanediol). As a result of the thus-obtained oil by HPLC (under Conditions 1), its area % was determined to be 99.4%. ($^1$H-NMR(CDCl$_3$): δ1.67-1.75(4H, m, —(C$\underline{H}_2$)$_2$—), δ2.35 (1H, s, O$\underline{H}$), δ3.52-3.56(2H, t, J=6.0 Hz, C$\underline{H}_2$), δ3.64-3.68 (2H, t, J=6.0 Hz, C$\underline{H}_2$), δ4.52(2H, s, C$\underline{H}_2$), δ7.27-7.31(1H, m, arom$\underline{H}$), δ7.66-7.70(1H, m, arom$\underline{H}$), δ8.52-8.56(2H, m, arom $\underline{H}$×2); MS(APCl):m/z=182[M+H]$^+$)

HPLC (Conditions 1)

Column: "INERTSIL ODS-3" (GL Sciences) 4.6 mmφ× 250 mm

Column temperature: constant temperature around 15° C.

Mobile phase:
A: 0.5% aqueous solution of ammonium acetate,
B: acetonitrile,
A:B=70:30 (fixed)
Flow rate: 1.0 mL/min
Detector: UV 254 nm
Injection volume: 20 μL Example 2

Synthesis of a compound (5-A) Represented by the following Structural Formula

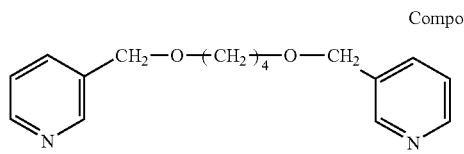

Compound (5-A)

The above-described compound (3-A) (5.0 g, 27.59 mmol) was added to DMF (25 mL), and under ice cooling, potassium tert-butoxide (3.1 g, 27.63 mmol) was added. To the resultant slurry, 3-chloromethylpyridine hydrochloride (0.5 g, 3.05 mmol) and potassium tert-butoxide (0.34 g, 3.03 mmol) were consecutively added at 5 to 6° C. That procedure was repeated 9 times, so that 3-chloromethylpyridine hydrochloride (4.5 g, 27.43 mmol) and potassium tert-butoxide (3.06 g, 27.27 mmol) were added in total.

After completion of the addition, the reaction mixture was analyzed by HPLC (under Conditions 1). As the peaks of 3-chloromethylpyridine and the compound (3-A) were confirmed, potassium tert-butoxide was added at below 5° C. until the peaks of 3-chloromethylpyridine and the compound (3-A) disappeared. The amount of the additional potassium tert-butoxide was 0.62 g (5.53 mmol).

The reaction mixture was subjected to solid-liquid separation, the resulting filter cake was washed with DMF (30 mL), and DMF was distilled off from the filtrate and washing under reduced pressure. Dichloromethane (20 mL) was added to the remaining concentrate. After the resulting solution was washed with a saturated aqueous solution of sodium chloride, the solvent was distilled off to obtain an oil (5.8 g). The crude product (0.5 g) was subjected to purification by chromatography on a silica gel column (developer: chloroform-methanol) to obtain the compound (5-A) in the form of an oil (0.3 g). ($^1$H-NMR: δ1.70-1.74(4H, m, —(C$\underline{H}_2$)$_2$—), δ3.50-3.54(4H, m, C$\underline{H}_2$×2), δ4.51(4H, s, C$\underline{H}_2$×2), δ7.25-7.29(2H, dd, J=4.9 Hz, 7.9 Hz, arom$\underline{H}$×2), δ7.65-7.69(2H, dt, J=1.7 Hz, 7.9 Hz, arom$\underline{H}$×2), δ8.52-8.57(4H, dd, J=1.7 Hz, 4.9 Hz, arom$\underline{H}$×4); MS(APCl):m/z=273[M+H]$^+$)

Example 3

Synthesis of a Compound (7-A) of the Following Structural Formula

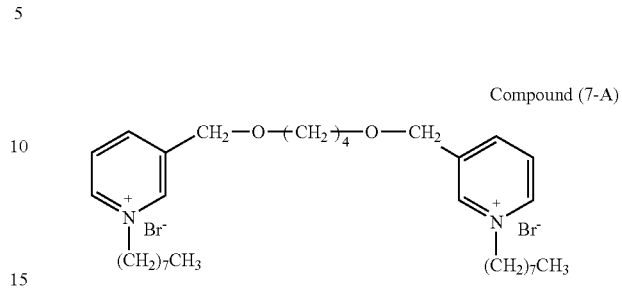

Compound (7-A)

Octyl bromide (35.5 g, 183.8 mmol) was added to the above-described compound (5-A) (5.0 g, 18.36 mmol), followed by a reaction at 70 to 80° C. for 20 hours.

When the reaction mixture was analyzed by HPLC (under Conditions 2), the peak of the compound (5-A) was no longer observed. From the reaction mixture, the upper layer, i.e., the octyl bromide layer was decanted out, and the lower layer, i.e., an oil was poured into a 1:3 (v/v) mixed solvent of acetonitrile and ethyl acetate. The resulting mixture was chilled. The precipitated crystals were collected at 0° C. by filtration and then dried under reduced pressure to obtain grayish white crystals (9.7 g, crude yield: 85% based on the compound (5-A)).

The thus-obtained crystals (2 g) were subjected to recrystallization from a 1:3 (v/v) mixed solvent of acetonitrile and ethyl acetate to obtain the compound (7-A) as slightly grayish white crystals (1.6 g). (m.p. 52 to 53° C., $^1$H-NMR(d$^6$-DMSO): δ0.82-0.89(6H, t, J=5.3 Hz, C$\underline{H}_3$×2), δ1.25-1.34 (20H, m, —(C$\underline{H}_2$)$_5$-×2), δ1.77-1.80(4H, m, —(C$\underline{H}_2$)$_2$-×2), δ2.04-2.09(4H, t, J=7.0 Hz, C$\underline{H}_2$×2), δ3.70-3.72(4H, t, J=5.9 Hz, C$\underline{H}_2$×2), δ4.67-4.71(4H, t, J=7.0 Hz, C$\underline{H}_2$×2), δ4.84 (4H, s, C$\underline{H}_2$×2), δ8.11-8.15(2H, dd, J=6.0 Hz, 8.0 Hz, arom$\underline{H}$×2), δ8.56-8.59(2H, d, J=8.0 Hz, arom$\underline{H}$×2), δ8.69-8.92(4H, dd, J=6.0 Hz, 13.1 Hz, arom$\underline{H}$×4); MS(ESI):m/z=579[M-Br]$^+$).

HPLC (Conditions 2)
Column: "INERTSIL ODS-3" (GL Sciences) 4.6 mmφ× 250 mm
Column temperature: constant temperature around 15° C.
Mobile phase:
A: 0.5% aqueous solution of ammonium acetate,
B: acetonitrile
A: 70% (held for 12 min)→(10 min)→A: 50% (held for 14 min)→A: 70%
Flow rate: 1.0 mL/min
Detector: UV 254 nm
Injection volume: 20 μL Example 4

Synthesis of the Compound (5-A): Dropwise addition of a Slurry of 3-chloromethylpyridine in DMF to a Slurry of 1,4-butanediol potassium salt in DMF 1,4-Butanediol (1.37 g, 15.20 mmol) was added to DMF (20 mL), and under ice cooling, potassium tert-butoxide (1.71 g, 15.24 mmol) was added, followed by stirring at room temperature for 1 hour.

On the side, 3-chloromethylpyridine hydrochloride (2.5 g, 15.24 mmol) was added to DMF (15 mL), and under ice cooling, potassium tert-butoxide (1.71 g, 15.24 mmol) was added. To the slurry of 1,4-butanediol in DMF, the slurry of 3-chloromethylpyridine in DMF was added dropwise at –17 to –14° C.

The reaction mixture was analyzed by HPLC (under Conditions 1). As the peak of 3-choloromethylpyridine was confirmed, potassium tert-butoxide was added at below –10° C. until the peak of 3-chloromethylpyridine disappeared. Subsequent to the confirmation of the disappearance of the peak of 3-chloromethylpyridine, potassium tert-butoxide (1.71 g, 15.24 mmol) was added to the reaction mixture under ice cooling, and a slurry of 3-chloromethylpyridine in DMF, the amount of which was the same as that prepared before, was added dropwise at –20 to –17° C. The reaction mixture was analyzed by HPLC (under Conditions 1). As the peak of 3-chloromethylpyridine was confirmed, potassium tert-butoxide was added at below –10° C. until the peak of 3-chloromethylpyridine disappeared. Subsequent to the confirmation of the disappearance of the peak of 3-chloromethylpyridine, the reaction mixture was subjected to solid-liquid separation, the filter cake was washed with DMF (25 mL), and DMF was then distilled off under reduced pressure from the filtrate and washing.

Dichloromethane (20 mL) was added to the remaining concentrate. After the resulting solution was washed with a saturated aqueous solution of sodium chloride, the solvent was distilled off to obtain the compound (5-A) in the form of an oil (3.79 g, crude yield: 91.8% based on 1,4-butanediol). As a result of an analysis of the thus-obtained oil by HPLC (under Conditions 1), the area % of the compound (5-A) was determined to be 64.5%.

Example 5

Synthesis of the Compound (5-A): Addition of potassium tert-butoxide in Portions to a Slurry of DMF, 1,4-butanediol and 3-chloromethylpyridine hydrochloride 1,4-Butanediol (1.37 g, 15.20 mmol) and 3-chloromethylpyridine hydrochloride (5.0 g, 30.48 mmol) were added to DMF (50 mL), and at –20 to –13° C., potassium tert-butoxide (6.84 g, 60.96 mmol) was added in 10 portions.

The reaction mixture was analyzed by HPLC (under Conditions 1). As the peak of 3-choloromethylpyridine and the peak of the compound (3-A) were confirmed, 3-chloromethylpyridine hydrochloride and potassium tert-butoxide were added at below –10° C. until the peak of 3-chloromethylpyridine and the peak of the compound (3-A) disappeared. The amount of the additional 3-chloromethylpyridine hydrochloride was 1.0 g (6.10 mmol), and that of the additional potassium tert-butoxide was 8.7 g (77.53 mmol).

The reaction mixture was subjected to solid-liquid separation, the filter cake was washed with DMF (25 mL), and DMF was then distilled off under reduced pressure from the filtrate and washing. Dichloromethane (20 mL) was added to the remaining concentrate. After the resulting solution was washed with a saturated aqueous solution of sodium chloride, the solvent was distilled off to obtain the compound (5-A) in the form of an oil (4.31 g, crude yield: 86.5% based on 3-chloromethylpyridine hydrochloride). As a result of an analysis of the thus-obtained oil by HPLC (under Conditions 1), the area % of the compound (5-A) was determined to be 72.8%.

Example 6

Synthesis of the Compound (5-A): Scale-up of Example 5

1,4-Butanediol (13.73 g, 0.1524 mol) and 3-chloromethylpyridine hydrochloride (50.0 g, 0.3048 mol) were added to DMF (250 mL), and at –19 to –12° C., potassium tert-butoxide (68.4 g, 0.6096 mol) was added in 20 portions.

The reaction mixture was analyzed by HPLC (under Conditions 1). As the peak of 3-choloromethylpyridine and the peak of the compound (3-A) were confirmed, 3-chloromethylpyridine hydrochloride and potassium tert-butoxide were added at below –10° C. until the peak of 3-chloromethylpyridine and the peak of the compound (3-A) disappeared.

The amount of the additional 3-chloromethylpyridine hydrochloride was 8.0 g (0.0366 mol), and that of the additional potassium tert-butoxide was 23.9 g (0.2130 mol). The reaction mixture was subjected to solid-liquid separation, the filter cake was washed with DMF (125 mL), and DMF was then distilled off under reduced pressure from the filtrate and washing. Dichloromethane (200 mL) was added to the remaining concentrate. After the resulting solution was washed with a saturated aqueous solution of sodium chloride, the solvent was distilled off to obtain the compound (5-A) in the form of an oil (41.0 g, crude yield: 98.8% based on 1,4-butanediol). As a result of an analysis of the thus-obtained oil by HPLC (under Conditions 1), the area % of the compound (5-A) was determined to be 68.8%.

Example 7

Synthesis of the Compound (5-A): Alternate Addition of 3-chloromethylpyridine hydrochloride and potassium tert-butoxide to a Slurry of 1,4-butanediol monopotassium salt in DMF 1,4-Butanediol (13.73 g, 0.1524 mol) was added to DMF (250 mL), and under ice cooling, potassium tert-butoxide (17.1 g, 0.1524 mol) was added, followed by stirring at room temperature for 2 hours. To the resulting slurry, 3-chloromethylpyridine hydrochloride (5.0 g, 30.48 mmol) and potassium tert-butoxide (3.42 g, 30.48 mmol) were consecutively added at –15 to –10° C. That procedure was repeated 5 times. As a subsequent addition, 3-chloromethylpyridine hydrochloride (5.0 g, 30.48 mmol) and potassium tert-butoxide (6.84 g, 60.96 mmol) were consecutively added at –16 to –7° C. That procedure was repeated 5 times. 3-Chloromethylpyridine hydrochloride and potassium tert-butoxide were, therefore, added in total amounts of 50.0 g (0.3048 mol) and 51.3 g (0.4572 mol), respectively.

Subsequent to the addition, the reaction mixture was analyzed by HPLC (under Conditions 1). As the peaks of 3-choloromethylpyridine and the compound (3-A) were confirmed, 3-chloromethylpyridine hydrochloride and potassium tert-butoxide were added at below 0° C. until the peaks of 3-chloromethylpyridine and the compound (3-A) disappeared.

The amount of the additional 3-chloromethylpyridine hydrochloride was 2.65 g (0.0366 mol), and that of the additional potassium tert-butoxide was 4.96 g (0.0442 mol). The reaction mixture was subjected to solid-liquid separation, the filter cake was washed with DMF (125 mL), and DMF was then distilled off under reduced pressure from the filtrate and washing.

Dichloromethane (200 mL) was added to the remaining concentrate. After the resulting solution was washed with a saturated aqueous solution of sodium chloride, the solvent was distilled off to obtain the compound (5-A) in the form of an oil (40.9 g, crude yield: 98.6% based on 1,4-butanediol). As a result of an analysis of the thus-obtained oil by HPLC (under Conditions 1), the area % of the compound (5-A) was determined to be 89.2%.

The thus-obtained crude product (2 g, 7.41 mmol) was dissolved in isopropyl alcohol (10 g), and into the resulting solution, hydrogen chloride gas (0.27 g, 7.41 mmol) was blown. The mixture was chilled to 10° C. The precipitated crystals were collected by filtration, and were then dried under reduced pressure to obtain the monohydrochloride of the compound (5-A) (1.1 g, yield: 48.0%). As a result of an analysis of the thus-obtained crystals by HPLC (under Conditions 1), the area % of the compound was determined to be 97.5%.

Example 8

Synthesis of the Compound (5-A): Production of the Compound (3-A) by Dropwise Addition of a Solution of 3-chloromethylpyridine hydrochloride in DMF to a Slurry of 1,4-butanediol and potassium tert-butoxide in DMF, and Subsequent Dropwise Addition of a Solution of potassium tert-butoxide in DMF to a Slurry Prepared by Adding 3-chloromethylpyridine hydrochloride to the Reaction Mixture 1,4-Butanediol (13.73 g, 0.1524 mol) was added to DMF (100 mL), and under ice cooling, potassium tert-butoxide (34.2 g, 0.3048 mmol) was added, followed by stirring at below 5° C. for 30minutes. To the resulting slurry, a solution of 3-chloromethylpyridine hydrochloride (25.0 g, 0.1524 mol) in DMF (150 mL) was added at 4 to 10° C. over 1.5 hours.

To the reaction mixture, 3-chloromethylpyridine hydrochloride (25.0 g, 0.1524 mol) and potassium tert-butoxide (17.1 g, 0.1524 mol) were then added at below 0° C. Subsequently, a solution of potassium tert-butoxide (17.1 g, 0.1524 mol) in DMF (100 mL) was added dropwise at −10 to 0° C. over 30 minutes. After completion of the dropwise addition, the reaction mixture was analyzed by HPLC (under Conditions 1). As the peaks of 3-choloromethylpyridine and the compound (3-A) were confirmed, 3-chloromethylpyridine hydrochloride and potassium tert-butoxide were added at below 0° C. until the peak of 3-chloromethylpyridine and the peak of the compound (3-A) disappeared.

The amount of the additional 3-chloromethylpyridine hydrochloride was 6.5 g (0.0396 mol), and that of the additional potassium tert-butoxide was 8.89 g (0.0792 mol). The reaction mixture was subjected to solid-liquid separation, the filter cake was washed with DMF (150 mL), and DMF was then distilled off under reduced pressure from the filtrate and washing. Dichloromethane (200 mL) was added to the remaining concentrate. After the resulting solution was washed with a saturated aqueous solution of sodium chloride, the solvent was distilled off to obtain the compound (5-A) in the form of an oil (43.2 g, crude yield: 92.1% based on 3-chloromethylpyridine hydrochloride). As a result of an analysis of the thus-obtained oil by HPLC (under Conditions 1), the area % of the compound (5-A) was determined to be 87.8%.

Example 9

Synthesis of the Compound (5-A): Dropwise Addition of a Solution of potassium tert-butoxide in DMF to a Slurry of 1,4-butanediol and 3-chloromethylpyridine hydrochloride in DMF 1,4-Butanediol (6.87 g, 0.0762 mol) and 3-chloromethylpyridine hydrochloride (25.0 g, 0.1524 mol) were added to DMF (200 mL), and at −11 to −5° C., a solution of potassium tert-butoxide (35.9 g, 0.3199 mol) in DMF (100 mL) was added over 1.5 hours. Subsequent to overnight aging at room temperature, the reaction mixture was analyzed by HPLC (under Conditions 1). As the peak of the compound (3-A) was confirmed, 3-chloromethylpyridine hydrochloride and potassium tert-butoxide were added at below 0° C. until the peak of the compound (3-A) disappeared. The amount of the additional 3-chloromethylpyridine hydrochloride was 2.5 g (0.0152 mol), and that of the additional potassium tert-butoxide was 3.42 g (0.0305 mol). The reaction mixture was subjected to solid-liquid separation, the filter cake was washed with DMF (150 mL), and DMF was then distilled off under reduced pressure from the filtrate and washing. Dichloromethane (100 mL) was added to the remaining concentrate. After the resulting solution was washed with a saturated aqueous solution of sodium chloride, the solvent was distilled off to obtain the compound (5-A) in the form of an oil (20.1 g, crude yield: 96.6% based on 1,4-butanediol). As a result of an analysis of the thus-obtained oil by HPLC (under Conditions 1), the area % of the compound (5-A) was determined to be 80.3%.

Example 10

Synthesis of the Compound (5-A): Scale-up of Example 7

1,4-Butanediol (41.2 g, 0.457 mol) was added to DMF (750 mL), and under ice cooling, potassium tert-butoxide (51.3 g, 0.457 mol) was added, followed by stirring at room temperature for 1 hour. To the resulting slurry, 3-chloromethylpyridine hydrochloride (7.5 g, 45.72 mmol) and potassium tert-butoxide (5.1 g, 45.45 mmol) were consecutively added at −5 to 0° C. That procedure was repeated 10 times. As a subsequent addition, 3-chloromethylpyridine hydrochloride (7.5 g, 45.72 mmol) and potassium tert-butoxide (10.2 g, 90.9 mmol) were consecutively added at −6 to −1° C. That procedure was repeated 10 times. 3-Chloromethylpyridine hydrochloride and potassium tert-butoxide were, therefore, added in total amounts of 150.0 g (0.9145 mol) and 153.0 g (1.364 mol), respectively.

Subsequent to the addition, the reaction mixture was analyzed by HPLC (under Conditions 1). As the peaks of 3-choloromethylpyridine and the compound (3-A) were confirmed, 3-chloromethylpyridine hydrochloride and potassium tert-butoxide were added at below 5° C. until the peaks of 3-chloromethylpyridine and the compound (3-A) disappeared. No additional 3-chloromethylpyridine hydrochloride was therefore incorporated, while the amount of the additional potassium tert-butoxide was 10.3 g (91.79 mmol). The reaction mixture was subjected to solid-liquid separation, the filter cake was washed with DMF (300 mL), and DMF was then distilled off under reduced pressure from the filtrate and washing. Dichloromethane (500 mL) was added to the remaining concentrate. After the resulting solution was washed with a saturated aqueous solution of sodium chloride, the solvent was distilled off to obtain the compound (5-A) in the form of an oil (111.9 g, crude yield: 89.9% based on 1,4-butanediol). As a result of an analysis of the thus-obtained oil by HPLC (under Conditions 1), the area % of the compound (5-A) was determined to be 93.9%.

Example 11

Synthesis of the Compound (7-A): Reaction Solvent: Mixed Solvent of Methanol and Acetonitrile The compound (5-A) (10.0 g, 36.72 mmol) and octyl bromide (70.9 g, 0.367 mol) were added to a 3:1 (v/v) mixed solvent (50 g) of methanol and acetonitrile, followed by a reaction under reflux for 135 hours. When the reaction mixture was analyzed by HPLC (under Conditions 2), the peak of the compound (5-A) was no longer observed. The upper layer, i.e., the octyl bromide layer was decanted out, and ethyl acetate was added to the lower layer. The resulting mixture was chilled, and the precipitated crystals were collected at –18° C. by filtration. The filter cake was washed with ethyl acetate (10 mL) and then dried under reduced pressure to obtain the compound (7-A) (20.3 g, crude yield: 83.9%). As a result of an analysis of the thus-obtained crystals by HPLC (under Conditions 2), the peak area % of the compound (7-A) was determined to be 91.4%.

Example 12

Synthesis of the Compound (7-A): Reaction Solvent: DMF

The compound (5-A) (5.0 g, 18.36 mmol) and octyl bromide (35.5 g, 0.184 mol) were added to DMF (25 mL), followed by a reaction at 50 to 55° C. for 86 hours. When the reaction mixture was analyzed by HPLC (under Conditions 2), the peak of the compound (5-A) was no longer observed. DMF and octyl bromide were distilled off under reduced pressure from the reaction mixture to obtain the compound (7-A) in the form of an oil (12.9 g, crude yield: 106.6%). As a result of an analysis of the thus-obtained oil by HPLC (under Conditions 2), the peak area % of the compound (7-A) was determined to be 93.0%.

Example 13

Synthesis of the Compound (7-A): Solventless Reaction, Reaction Temperature: 45 to 55° C.

Octyl bromide (70.9 g, 0.3671 mol) was added to the compound (5-A) (10.0 g, 36.72 mmol), followed by a reaction at 49 to 52° C. for 50 hours. When the reaction mixture was analyzed by HPLC (under Conditions 2), the peak of the compound (5-A) was no longer observed. The reaction mixture was chilled. The precipitated crystals were collected at room-temperature by filtration, washed with ethyl acetate (20 mL), and then dried under reduced pressure to obtain the compound (7-A) (21.2 g, crude yield: 87.6%). As a result of an analysis of the thus-obtained crystals by HPLC (under Conditions 2), the peak area % of the compound (7-A) was determined to be 93.3%.

Example 14

Synthesis of the Compound (7-A): Solventless Reaction, Reaction Temperature: 75 to 80° C., Crystallization from a Mixed Solvent of Ethanol and Ethyl Acetate Octyl bromide (70.9 g, 0.3671 mol) was added to the compound (5-A) (10.0 g, 36.72 mmol), followed by a reaction at 75 to 77° C. for 20 hours. When the reaction mixture was analyzed by HPLC (under Conditions 2), the peak of the compound (5-A) was no longer observed. The upper layer, i.e., the octyl bromide layer was decanted out from the reaction mixture, and ethanol (10 mL) was added to the lower layer to effect dissolution. The resulting solution was poured into ethyl acetate (200 mL). The resulting mixture was chilled. The precipitated crystals were collected at –10° C. by filtration, washed with ethyl acetate (10 mL), and then dried under reduced pressure to obtain the compound (7-A) (17.4 g, crude yield: 71.9%). As a result of an analysis of the thus-obtained crystals by HPLC (under Conditions 2), the peak area % of the compound (7-A) was determined to be 95.2%.

Example 15

Synthesis of the Compound (7-A): Conducted in a Similar Manner as in Example 14 Except that the Ratio of Ethanol to Ethyl Acetate in the Mixed Solvent was Changed and the Reaction Conditions were Modified as will be Described Below Octyl bromide (70.9 g, 0.3671 mol) was added to the compound (5-A) (10.0 g, 36.72 mmol), followed by a reaction at 75 to 77° C. for 20 hours. When the reaction mixture was analyzed by HPLC (under Conditions 2), the peak of the compound (5-A) was no longer observed. When ethanol (10 mL) was added to the reaction mixture and the resulting mixture was allowed to stand, the mixture separated into a layer of a solution of the compound (7-A) in ethanol as an upper layer and an octyl bromide layer as a lower layer. The lower layer was separated out. The upper layer was then poured into ethyl acetate (500 mL). The resulting mixture was chilled. The precipitated crystals were collected at 5° C. by filtration, washed with ethyl acetate (10 mL), and then dried under reduced pressure to obtain the compound (7-A) (20.8 g, crude yield: 86.0%). As a result of an analysis of the thus-obtained crystals by HPLC (under Conditions 2), the peak area % of the compound (7-A) was determined to be 90.8%.

Example 16

Synthesis of the Compound (7-A): Conducted in a Similar Manner as in Example 14 Except that the Ratio of Ethanol to Ethyl Acetate in the Mixed Solvent was Changed and the Reaction Conditions were Modified as will be Described Below. Crude Product was Recrystallized from a Mixed Solvent of Acetonitrile and Ethyl Acetate.

Octyl bromide (709.1 g, 3.67 mol) was added to the compound (5-A) (100.0 g, 0.367 mol), followed by a reaction at 75 to 78° C. for 20 hours. When the reaction mixture was analyzed by HPLC (under Conditions 2), the peak of the compound (5-A) was no longer observed. When ethanol (97 mL) was added to the reaction mixture and the resulting mixture was allowed to stand, the mixture separated into a layer of a solution of the compound (7-A) in ethanol as an upper layer and an octyl bromide layer as a lower layer. The lower layer was separated out. The upper layer was then poured into ethyl acetate (2900 mL). The resulting mixture was chilled. The precipitated crystals were collected at 3° C. by filtration, washed with ethyl acetate (100 mL), and then dried under reduced pressure to obtain the compound (7-A) (215.8 g, crude yield: 89.3%). As a result of an analysis of the thus-obtained crystals by HPLC (under Conditions 2), the peak area % of the compound (7-A) was determined to be 93.1%.

The thus-obtained crystals (212 g) was recrystallized from a mixed solvent of acetonitrile (592 mL) and ethyl acetate (1953 mL) to obtain the compound (7-A) (192.1 g, purification yield: 90.6%). As a result of an analysis of the thus-obtained crystals by HPLC (under Conditions 2), the peak area % of the compound (7-A) was determined to be 96.4%.

Example 17

Synthesis of the Compound (7-A): Synthesis of the Compound (5-A) from 3-chloromethylpyridine benzenesulfonate. Synthesis of the Compound (7-A) without Isolation of the Compound (5-A)

1,4-Butanediol (3.2 g, 0.035 mol) was added to DMF (35 g), followed by the addition of potassium tert-butoxide (3.9 g, 0.035 mol) at 10 to 20° C. To the resulting slurry, a solution of 3-chloromethylpyridine benzenesulfonate (20.0 g, 0.07 mol) in DMF (55 g) was added dropwise, and at the same time, potassium tert-butoxide (16.8 g, 0.15 mol) was added in portions, both at 10 to 25° C. Subsequent to the completion of the addition, the reaction mixture was analyzed by HPLC (under Conditions 1). As the peaks of 3-choloromethylpyridine and the compound (3-A) were confirmed, potassium tert-butoxide was added at below 20° C. until the peaks of 3-chloromethylpyridine and the compound (3-A) disappeared. The amount of the additional potassium tert-butoxide was 1.5 g (0.01 mol).

The inorganic salt was filtered off from the reaction mixture, and the filter cake was washed with DMF (10 g). Octyl bromide (96.0 g, 0.5 mol) was added to the filtrate and washing, followed by a reaction at 60° C. for 72 hours. When the reaction mixture was analyzed by HPLC (under Conditions 2), the peak of the compound (5-A) was no longer observed. The reaction mixture was subjected to solid-liquid separation, and the filter cake was washed with DMF (20 g). From the filtrate and washing, DMF and octyl bromide were distilled off under reduced pressure to obtain the compound (7-A) in the form of an oil (41.1 g, crude yield: 89.2% based on 3-chloromethylpyridine benzenesulfonate). As a result of an analysis of the thus-obtained oil by HPLC (Conditions 2), the peak area % of the compound (7-A) was determined to be 87.8%.

Example 18

Synthesis of the Compound (5-A): Conducted in a Similar Manner as in Example 7 Except that the Base was Changed to sodium tert-butoxide and the Reaction Conditions were Modified as will be Described Below 1,4-Butanediol (13.73 g, 0.1524 mol) was added to DMF (250 mL), and under ice cooling, sodium tert-butoxide (14.65 g, 0.1524 mol) was added, followed by stirring at room temperature for 1 hour. To the resulting slurry, 3-chloromethylpyridine hydrochloride (5.0 g, 30.48 mmol) and sodium tert-butoxide (2.93 g, 30.48 mmol) were consecutively added at −15 to −10° C. That procedure was repeated 5 times. As a subsequent addition, 3-chloromethylpyridine hydrochloride (5.0 g, 30.48 mmol) and sodium tert-butoxide (5.86 g, 60.97 mmol) were consecutively added at −16 to −7° C. That procedure was repeated 5 times. 3-Chloromethylpyridine hydrochloride and sodium tert-butoxide were, therefore, added in total amounts of 50.0 g (0.3048 mol) and 43.95 g (0.4573 mol), respectively.

Subsequent to the addition, the reaction mixture was analyzed by HPLC (under Conditions 1). As the peaks of 3-choloromethylpyridine and the compound (3-A) were confirmed, 3-chloromethylpyridine hydrochloride and sodium tert-butoxide were added at below 0° C. until the peaks of 3-chloromethylpyridine and the compound (3-A) disappeared. The amount of the additional 3-chloromethylpyridine hydrochloride was 2.5 g (0.0152 mol), and that of the additional sodium tert-butoxide was 2.93 g (0.0305 mol). The reaction mixture was subjected to solid-liquid separation, the filter cake was washed with DMF (125 mL), and DMF was then distilled off under reduced pressure from the filtrate and washing. Dichloromethane (200 mL) was added to the remaining concentrate. After the resulting solution was washed with a saturated aqueous solution of sodium chloride, the solvent was distilled off to obtain the compound (5-A) in the form of an oil (39.4 g, crude yield: 94.9% based on 1,4-butanediol). As a result of an analysis of the thus-obtained oil by HPLC (under Conditions 1), the area % of the compound (5-A) was determined to be 88.3%.

Example 19

Synthesis of the Compound (5-A): Reaction Making Use of 3-pyridinemethanol benzenesulfonate 1,4-Butanediol (0.9 g, 9.99 mmol) was added to DMF (15 mL), and under ice cooling, potassium tert-butoxide (1.13 g, 10.07 mmol) was added, followed by stirring at room temperature for 1 hour. To the resulting slurry, a solution of 3-pyridinemethanol benzenesulfonate (2.5 g, 10.03 mmol) in DMF (5 mL) was added dropwise at −5 to 0° C. After stirring at −5 to 0° C. for 30 minutes, potassium tert-butoxide (1.13 g, 10.07 mmol) was added at −5 to −0° C. to the reaction mixture. A solution of 3-pyridinemethanol benzenesulfonate (2.5 g, 10.03 mmol) in DMF (5 mL) was added dropwise at −5 to −0° C. to the resulting slurry.

Subsequent to the dropwise addition, the reaction mixture was analyzed by HPLC (under Conditions 1). As the peaks of 3-pyridinemethanol benzenesulfonate and the compound (3-A) were confirmed, 3-pyridinemethanol benzenesulfonate and potassium tert-butoxide were added at below 0° C. until the peaks of 3-pyridinemethanol benzenesulfonate and the compound (3-A) disappeared. The amount of the additional 3-pyridinemethanol benzenesulfonate was 0.25 g (1.00 mmol), and that of the additional potassium tert-butoxide was 0.22 g (1.96 mmol). The reaction mixture was subjected to solid-liquid separation, the filter cake was washed with DMF (10 mL), and DMF was then distilled off under reduced pressure from the filtrate and washing. Dichloromethane (20 mL) was added to the remaining concentrate. After the resulting solution was washed with a saturated aqueous solution of sodium chloride, the solvent was distilled off to obtain the compound (5-A) in the form of an oil (2.4 g, crude yield: 88.2% based on 1,4-butanediol). As a result of an analysis of the thus-obtained oil by HPLC (under Conditions 1), the area % of the compound (5-A) was determined to be 85.8%.

Example 20

Synthesis of a Compound (3-B) Represented by the Following Structural Formula: Conducted in a Similar Manner as in Example 1 Except that 3-chloromethylpyridine hydrochloride was Changed to 4-chloromethylpyridine hydrochloride and the Reaction Conditions were Modified as will be Described Below

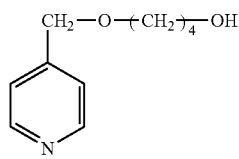

Compound (3-B)

1,4-Butanediol (8.24 g, 91.43 mmol) was added to DMF (75 mL), and under ice cooling, potassium tert-butoxide (10.3 g, 91.79 mmol) was added, followed by stirring at room temperature for 1 hour. To the resultant slurry, 4-chloromethylpyridine hydrochloride (1.5 g, 9.14 mmol) and potassium tert-butoxide (1.03 g, 9.18 mmol) were consecutively added at −10 to −5° C. That procedure was repeated 10 times.

After completion of the addition, the reaction mixture was analyzed by HPLC (under Conditions 1). As the peak of 4-chloromethylpyridine was confirmed, potassium tert-butoxide was added at below 10° C. until the peak of 4-chloromethylpyridine disappeared. The amount of the additional potassium tert-butoxide was 1.03 g (9.18 mmol) The reaction mixture was subjected to solid-liquid separation, the resulting filter cake was washed with DMF (20 mL), and DMF was distilled off from the filtrate and washing under reduced pressure to obtain a crude product in the form of an oil (17.0 g). As a result of an analysis of the thus-obtained oil by HPLC (under conditions 1), the area % of the compound (3-B) was determined to be 63.0%.

The crude product was dissolved in water (30 mL), and was then washed with toluene. Subsequently, sodium chloride (6 g) was added to the water layer, followed by extraction with dichloromethane (20 mL×2). The extracts were dried over anhydrous magnesium sulfate, and the solvent was then distilled off to obtain the compound (3-B) in the form of an oil (9.21 g, yield: 57.2% based on 1,4-butanediol). As a result of the thus-obtained oil by HPLC (under Conditions 1), its area % was determined to be 99.4%. ($^1$H-NMR(CDCl$_3$) δ1.65-1.80(4H, m, —(CH$_2$)$_2$—), δ2.4(1H, s, OH), δ3.54-3.58(2H, t, J=5.9 Hz, CH$_2$), δ3.66-3.70(2H, t, J=5.9 Hz, CH$_2$), δ4.53(2H, s, CH$_2$), δ7.24-7.26(2H, dd, J=1.5 Hz, 4.5 Hz, aromH×2), δ8.55-8.57(2H, dd, J=1.5 Hz, 4.5 Hz, aromH×2); MS(APCI): m/z=182[M+H]$^+$)

Example 21

Synthesis of the Compound (5-B) Represented by the Following Structural Formula: Conducted in a Similar Manner as in Example 7 Except that 3-chloromethylpyridine hydrochloride was Changed to 4-chloromethylpyridine hydrochloride and the Reaction Conditions were Modified as will be Described Below

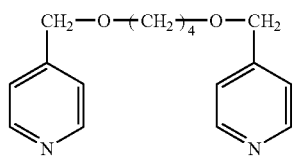

Compound (5-B)

1,4-Butanediol (2.7 g, 30.0 mmol) was added to DMF (49 mL), and under ice cooling, potassium tert-butoxide (3.4 g, 30.0 mmol) was added, followed by stirring at room temperature for 1 hour. To the resulting slurry, 4-chloromethylpyridine hydrochloride (0.98 g, 6 mmol) and potassium tert-butoxide (0.68 g, 6 mmol) were consecutively added at −5 to −3° C. That procedure was repeated 5 times. As a subsequent addition, 4-chloromethylpyridine hydrochloride (0.98 g, 6 mmol) and potassium tert-butoxide (1.36 g, 12 mmol) were consecutively added at −5 to −2° C. That procedure was repeated 5 times. 4-Chloromethylpyridine hydrochloride and potassium tert-butoxide were, therefore, added in total amounts of 9.8 g (60 mmol) and 10.2 g (90 mmol), respectively.

Subsequent to the addition, the reaction mixture was analyzed by HPLC (under Conditions 1). As the peaks of 3-choloromethylpyridine and the compound (3-B) were confirmed, 4-chloromethylpyridine hydrochloride and potassium tert-butoxide were added at below 10° C. until the peaks of 4-chloromethylpyridine and the compound (3-B) disappeared. The amount of the additional 4-chloromethylpyridine hydrochloride was 2.0 g (12 mmol), and that of the additional potassium tert-butoxide was 2.6 g (24 mmol). The reaction mixture was subjected to solid-liquid separation, the filter cake was washed with DMF (20 mL), and DMF was then distilled off under reduced pressure from the filtrate and washing.

Ethyl acetate (50 mL) was added to the remaining concentrate. After the resulting solution was washed with water, the solvent was distilled off to obtain the compound (5-B) in the form of yellow crystals. As a result of an analysis of the thus-obtained crystals of the compound by HPLC (under Conditions 1), the area % of the compound (5-B) was determined to be 70.5%. The thus-obtained crude product (5 g, 18 mmol) was recrystallized from isopropyl alcohol (23.3 g) to obtain the compound (5-B) in the form of white crystals (2.7 g) (m.p. 98.6 to 100.2° C., $^1$H-NMR(CDCl$_3$): δ1.75-1.79(4H, m, —(CH$_2$)$_2$—), δ3.53-3.57(4H, m, CH$_2$×2), δ4.52(4H, s, CH$_2$×2), δ7.23-7.27(4H, dd, J=0.8 Hz, 6.0 Hz, aromH×4), δ8.55-8.57(4H, dd, J=1.6 Hz, 6.0 Hz, aromH×4); MS(APCI): m/z=273[M+H]$^+$)

Example 22

Synthesis of a Compound (7-B) of the Following Structural Formula: Conducted in a Similar Manner as in Example 3 Except that the Compound (5-B) was Changed to one Derived from 4-chloromethylpyridine hydrochloride and the Reaction Conditions were Modified as will be Described Below

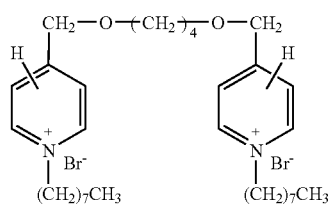

Compound (7-B)

Octyl bromide (21.3 g, 110.3 mmol) was added to the above-described compound (5-B) (2.0 g, 7.34 mmol), followed by a reaction at 70 to 80° C. for 53 hours. When the reaction mixture was analyzed by HPLC (under Conditions 2), the peak of the compound (5-B) was no longer observed. Octyl bromide was distilled off under reduced pressure from the reaction mixture to obtain the compound (7-B) in the form of an oil (5.2 g, crude yield: 107.7%). As a result of an analysis of the thus-obtained oil by HPLC (under Conditions 2), the peak area of the compound (7-B) was determined to be 81.3%.

Example 23

Purification of the Compound (5-B): Purification Through a Hydrochloride (the Molar Ratio of Hydrochloric Acid to the Compound (5-B): 1.5)

The compound (5-B) (5.0 g, 18.36 mmol, area ratio: 90.5%) was dissolved in isopropyl alcohol (15.0 g), and into the resulting solution, hydrogen chloride gas (1.01 g, 27.70 mmol) was blown at 20 to 40° C. The mixture was chilled to 10° C. The precipitated crystals were collected by filtration, and were then dried under reduced pressure to obtain the dihydrochloride of the compound (5-B) (4.4 g, yield: 69.8%). As a result of an analysis of the thus-obtained crystals by HPLC (under Conditions 1), the area % of the compound (5-B) was determined to be 97.9%.

Example 24

Purification of the Compound (5-B): Purification Through a Hydrochloride (the Molar Ratio of Hydrochloric Acid to the Compound (5-B): 2.0)

The compound (5-B) (5.0 g, 18.36 mmol, area ratio: 90.5%) was dissolved in isopropyl alcohol (15.0 g), and into the resulting solution, hydrogen chloride gas (1.34 g, 36.75 mmol) was blown at 20 to 40° C. The mixture was chilled to 10° C. The precipitated crystals were collected by filtration, and were then dried under reduced pressure to obtain the dihydrochloride of the compound (5-B) (5.7 g, yield: 90.5%). As a result of an analysis of the thus-obtained crystals by HPLC (under Conditions 1), the area % of the compound (5-B) was determined to be 96.1%.

Example 25

Purification of the Compound (5-B): Conducted in a Similar Manner as in Example 23 Except that the Blowing Temperature of Hydrogen Chloride was changed to 60 to 65° C. and the Reaction Conditions were Modified as will be Described Below The compound (5-B) (15.0 g, 55.08 mmol, area ratio: 90.5%) was dissolved in isopropyl alcohol (45.0 g), and into the resulting solution, hydrogen chloride gas (4.0 g, 0.1097 mol) was blown at 60 to 65° C. The mixture was chilled to 5° C. The precipitated crystals were collected by filtration, and were then dried under reduced pressure to obtain the dihydrochloride of the compound (5-B) (17.2 g, yield: 90.5%). As a result of an analysis of the thus-obtained crystals by HPLC (under Conditions 1), the area % of the compound (5-B) was determined to be 97.9%.

Example 26

Purification of the Compound (5-B): Purification Through a Sulfate (the Molar Ratio of Sulfuric Acid to the Compound (5-B): 1.0)

The compound (5-B) (15.0 g, 55.08 mmol, area ratio: 90.5%) was dissolved in isopropyl alcohol (22.5 g), and into the resulting solution, 98% sulfuric acid (5.5 g, 54.96 mmol) was added dropwise at 70 to 75° C. The mixture was chilled to 5° C. The precipitated crystals were collected by filtration, and were then dried under reduced pressure to obtain the disulfate of the compound (5-B) (17.2 g, yield: 47.5%). As a result of an analysis of the thus-obtained crystals by HPLC (under Conditions 1), the area % of the compound (5-B) was determined to be 94.6%.

Example 27

Purification of the Compound (5-B): Purification Through a Sulfate (the Molar Ratio of Sulfuric Acid to the Compound (5-B): 1.5)

The compound (5-B) (10.0 g, 36.72 mmol, area ratio: 90.5%) was dissolved in isopropyl alcohol (20 mL), and into the resulting solution, 98% sulfuric acid (5.5 g, 54.96 mmol) was added dropwise at 45 to 60° C. The mixture was chilled to 5° C. The precipitated crystals were collected by filtration, and were then dried under reduced pressure to obtain the disulfate of the compound (5-B) (10.6 g, yield: 61.6%). As a result of an analysis of the thus-obtained crystals by HPLC (under Conditions 1), the area % of the compound (5-B) was determined to be 94.9%.

Example 28

Purification of the Compound (5-B): Purification Through a Sulfate (the Molar Ratio of Sulfuric Acid to the Compound (5-B): 2.0)

The compound (5-B) (20.0 g, 73.43 mmol, area ratio: 90.5%) was dissolved in isopropyl alcohol (40 mL), and into the resulting solution, 98% sulfuric acid (14.7 g, 0.1468 mol)

was added dropwise at 60 to 80° C. The mixture was chilled to 5° C. The precipitated crystals were collected by filtration, and were then dried under reduced pressure to obtain the disulfate of the compound (5-B) (27.5 g, yield: 79.9%). As a result of an analysis of the thus-obtained crystals by HPLC (under Conditions 1), the area % of the compound (5-B) was determined to be 94.7%.

Example 29

Synthesis of the Compound (5-B): Concurrent Dropwise Addition of a Slurry of 4-chloromethylpyridine hydrochloride in DMF and a Slurry of sodium tert-butoxide in DMF to a Slurry of the Monosodium Salt of 1,4-butanediol 1,4-Butanediol (8.43 g, 0.0935 mol) was added to DMF (80 mL), and under ice cooling, sodium tert-butoxide (9.0 g, 0.0936 mmol) was added, followed by stirring at room temperature for 1 hour. To the resulting slurry, a slurry of 4-chloromethylpyridine hydrochloride (34.1 g, 45.72 mmol) in DMF (100 mL) and a slurry of sodium tert-butoxide (37.0 g, 0.3850 mol) in DMF (60 mL) were added at 0 to 50° C. concurrently.

Subsequent to the completion of the dropwise addition, a reaction was conducted at room temperature for 1 hour. The reaction mixture was analyzed by HPLC (under Conditions 1). The peak of 4-chloromethylpyridine was not detected, and the peak of the compound (3-B) was no longer observed practically. The reaction mixture was subjected to solid-liquid separation, the filter cake was washed with DMF (60 mL), and DMF was distilled off under reduced pressure from the filtrate and washing. Isopropyl alcohol (84.9 g) was added to the remaining liquid (28.3 g) to effect dissolution. Into the resulting solution, hydrogen chloride gas (6.9 g, 0.1892 mol) was blown at 60 to 65° C. The mixture was chilled to 5° C. The precipitated crystals were collected by filtration, and were then washed with isopropyl alcohol (14.2 mL) to obtain a wet cake (36.1 g) of the dihydrochloride of the compound (5-B). The thus-obtained wet cake was dissolved in water (18.1 g). The resulting solution was adjusted to pH 10 to 11.5 with liquid caustic soda, and was then extracted with toluene (100 mL). After the toluene layer was washed with water (20 mL), toluene was distilled off under reduced pressure to obtain the compound (5-B) in the form of an oil (22.2 g, yield: 87.2% based on 1,4-butanediol). As a result of an analysis of the thus-obtained oil by HPLC (under Conditions 1), the area % of the compound (5-B) was determined to be 97.5%.

Example 30

1,4-Butanediol (4.5 g, 0.05 mol) and benzyltriethylammonium chloride (phase transfer catalyst) (20 mg) were added to water (10 mL), and under ice cooling, a 48 wt. % aqueous solution of sodium hydroxide (8.3 g, 0.1 mol) was added, followed by aging at 5 to 15° C. for 1 hour. Subsequent to the aging, 3-chloromethylpyridine hydrochloride (8.2 g, 0.05 mol) was added, followed by a reaction at 5 to 15° C. for 10 hours. As a result of an analysis of the reaction mixture by HPLC, the area of the resulting compound (same as the compound 3-B) was determined to be 47% while the area of the compound (same as the compound 5-B) was determined to be 30%. Further, 3-chloromethylpyridine hydrochloride (8.2 g, 0.05 mol) was added, and a 48 wt. % aqueous solution of sodium hydroxide (8.3 g, 0.1 mol) was added dropwise over 10 hours. As a result of an analysis of the reaction mixture by HPLC, the area of the compound (3-B) was determined to be 2% while the area of the resulting compound (same as the compound 5-B) was determined to be 79%. That reaction mixture was extracted with toluene (50 mL×2), and the thus-obtained toluene solution was concentrated under reduced pressure to obtain an oil (Compound 5-B) (15.3 g). As a result of an analysis of the thus-obtained oil by HPLC, the area of the compound (5-B) was determined to be 87%.

Example 31

Synthesis of the Compound (7-B): Conducted in a Similar Manner as in Example 14 Except That the Compound (5-B) was Used in a Purified form and the Reaction Conditions were Modified as will be Described Below Octyl bromide (141.8 g, 0.7343 mol) was added to the compound (5-B) (20.0 g, 0.0734 mol, HPLC (under Conditions 1): 98.2 area %), followed by a reaction at 75 to 78° C. for 20.5 hours. When the reaction mixture was analyzed by HPLC (under Conditions 2), the peak of the compound (5-B) was no longer observed. When acetonitrile (19.3 mL) was added to the reaction mixture and the resulting mixture was allowed to stand, the mixture separated into a layer of a solution of the compound (7-B) in acetonitrile as an upper layer and an octyl bromide layer as a lower layer. The lower layer was separated out. The upper layer was then concentrated at 80° C. under reduced pressure up to 10 Torr to obtain the compound (7-B) in the form of an oil (44.9 g, crude yield: 93.0%). As a result of an analysis of the thus-obtained oil by HPLC (under Conditions 2), the peak area % of the compound (7-B) was determined to be 97.5%. ($^1$H-NMR (d$^6$-DMSO): δ0.86-0.90(6H, t, J=5.5 Hz, C$\underline{H}_3$×2), δ1.26-1.35 (20H, m, —(C$\underline{H}_2$)$_5$—×2), δ1.80-1.85(4H, m, —(C$\underline{H}_2$)$_2$—×2), δ2.05-3.02(4H, m, C$\underline{H}_2$×2), δ3.72-3.75(4H, m, C$\underline{H}_2$×2), δ4.68-4.72(4H, m, C$\underline{H}_2$×2), δ4.85(4H, s, C$\underline{H}_2$×2), δ8.13(4H, dd, J=0.8 Hz, 6.5 Hz, arom$\underline{H}$×4), δ8.85(4H, dd, J=1.6 Hz, 6.5 Hz, arom$\underline{H}$×4)

Example 32

Synthesis of a Compound (7-C) of the Following Structural Formula

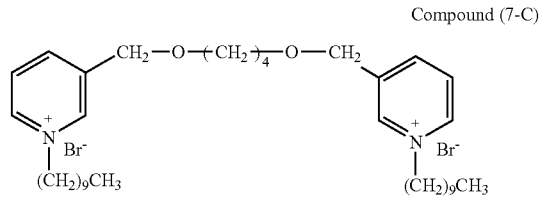

Compound (7-C)

Decyl bromide (40.6 g, 183.8 mmol) was added to the above-described compound (5-A) (5.0 g, 18.36 mmol), followed by a reaction at 70 to 80° C. for 20 hours.

When the reaction mixture was analyzed by HPLC (under Conditions 2), the peak of the compound (5-A) was no longer observed. From the reaction mixture, the upper layer, i.e., the decyl bromide layer was decanted out, and the lower layer, i.e., an oil was poured into a 1:3 (v/v) mixed solvent of acetonitrile and ethyl acetate. The resulting mixture was chilled. The precipitated crystals were collected at 0° C. by filtration and then dried under reduced pressure to obtain grayish white crystals (11.6 g, crude yield: 88.5% based on the compound (5-A)). As a result of an analysis of the crystals of the compound by HPLC (under Conditions 1), the area % of the compound (7-C) was determined to be 98.4%. Its melting point, NMR analysis data and elemental analysis data were as follows.

(m.p. 76.8 to 79.2° C., $^1$H-NMR(CD$_3$OD): δ0.9(6H, t, C$\underline{H}_3$×2), δ1.29-1.40(28H, m, (C$\underline{H}_2$)$_7$×2), δ1.77-1.84(4H, m, C$\underline{H}_2$×2), δ2.00-2.05(4H, t, C$\underline{H}_2$×2), δ3.69-3.70(4H, t, C$\underline{H}_2$×2), δ4.64-4.68(4H, t, C$\underline{H}_2$×2), δ4.77(4H, s, C$\underline{H}_2$×2), δ8.07-8.11 (2H, dd, J=, arom$\underline{H}$×2), δ8.55-8.57(2H, d, arom$\underline{H}$×2), δ8.93-8.94(2H, d, arom$\underline{H}$×2), δ9.02(2H, s, arom$\underline{H}$×2)

| Elemental analysis | | | |
|---|---|---|---|
| | C | H | N |
| Calculated (%) | 60.50 | 8.74 | 3.92 |
| Found (%) | 60.29 | 8.65 | 3.89 |

HPLC (Conditions 2)

Column: "INERTSIL ODS-3" (GL Sciences) 4.6 mmφ×250 mm

Column temperature: constant temperature around 15° C.

Mobile phase:
  A: 0.5% aqueous solution of ammonium acetate,
  B: acetonitrile
  A: 60% (held for 5 min)→(10 min)→A: 30% (held for 30 min)→A: 60%

Flow rate: 1.0 mL/min

Detector: UV 254 nm

Injection volume: 10 μL

Example 33

In a similar manner as in Example 32 except that an equivalent molar amount of dodecyl bromide was used in place of decyl bromide, a compound (7-D) was obtained (13.0 g, crude yield: 91.5%). As a result of an analysis of the thus-obtained compound (7-D) by HPLC (under Conditions 3), the peak area % of the compound (7-D) was determined to be 97.5%. Its melting point, NMR analysis data and elemental analysis data were as follows.

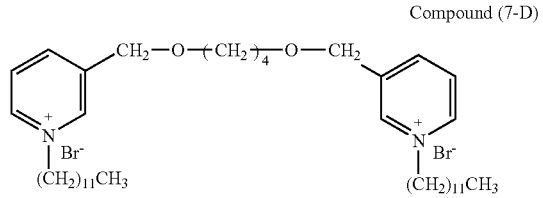

Compound (7-D)

(m.p. 90.0 to 91.4° C., $^1$H-NMR(CD$_3$OD): δ0.89(6H, t, C$\underline{H}_3$×2), δ1.26-1.39(36H, m, (C$\underline{H}_2$)$_9$×2), δ1.79-1.82(4H, m, C$\underline{H}_2$×2), δ1.84-2.05(4H, m, C$\underline{H}_2$×2), δ3.67-3.70(4H, t, C$\underline{H}_2$×2), δ4.65-4.68(4H, t, C$\underline{H}_2$×2), δ4.77(4H, s, C$\underline{H}_2$×2), δ8.07-8.11(2H, dd, arom$\underline{H}$×2), δ8.55-8.57(2H, d, arom$\underline{H}$×2), δ8.93-8.94(2H, d, arom$\underline{H}$×2), δ9.02(2H, s, arom$\underline{H}$×2)

| Elemental analysis | | | |
|---|---|---|---|
| | C | H | N |
| Calculated (%) | 62.33 | 9.15 | 3.63 |
| Found (%) | 62.14 | 9.12 | 3.61 |

HPLC (Conditions 3)

Column: "CAPCELL PAK C$_{18}$ SG120" (Shiseido)
  4.6 mmφ×250 mm

Column temperature: constant temperature around 15° C.

Mobile phase:
  A: 0.1 M aqueous solution of potassium dihydrogenphosphate (0.05% phosphoric acid),
  B: 80% aqueous solution of acetonitrile
  A:B=30:70

Flow rate: 1.0 mL/min

Detector: UV 254 nm

Injection volume: 20 μL

Test 1

Bacteriostatic Activities of the Above-Described Invention Compounds (7-A to 7-D) Against Various Bacteria Using benzalkonium chloride as a control compound, minimum inhibitory concentrations (MICs) were determined.

Each minimum inhibitory concentration (MIC) was determined as will be described hereinafter. Aliquots of a suspension of stationary-phase cells, the cell concentration of which had been adjusted to 10$^6$ cells/mL with nutrient broth in accordance with the general broth dilution method, were mixed with serially-diluted solutions of a compound, respectively. Subsequent to stationary culture at 37° C. for 24 hours, the MIC value was determined depending upon whether or not any growth had taken place.

As test microorganisms, ten (10) Gram-negative bacteria and six (6) Gram-positive bacteria were used. The results are presented in Table 1.

TABLE 1

Bacteriostatic Spectra

| | MIC (μM) | | | | Control |
|---|---|---|---|---|---|
| | Compound | | | | |
| Test microorganism: bacteria | 7-A | 7-B | 7-C | 7-D | comp'd$^{a)}$ |
| Pseudomonas aeruginosa ATCC 27583 | 6.25 | 3.6 | 1.8 | 0.9 | 51.2 |
| Pseudomonas aeruginosa ATCC 10145 | 6.25 | 3.6 | 1.8 | 0.9 | 51.2 |
| Pseudomonas aeruginosa ATCC 3080 | 6.25 | 6.25 | 0.9 | 0.9 | 102.4 |
| Klebsiella pneumoniae ATCC 4352 | 1.8 | 1.8 | 0.45 | 0.2 | 12.8 |
| Klebsiella pneumoniae ATCC 13883 | 1.8 | 3.6 | 1.8 | 0.9 | 102.4 |
| Proteus rettgeri NIH 96 | 3.6 | 3.6 | 0.9 | 0.9 | 51.2 |
| Proteus vulgaris ATCC 13315 | 3.6 | 3.6 | 0.45 | 0.2 | 16.4 |
| Proteus mirabilis IFO 3849 | 6.25 | 6.25 | 1.8 | 1.8 | 204.8 |
| Escherichia coli K12 OUT 8401 | 0.9 | 0.9 | 0.45 | 0.2 | 12.8 |

TABLE 1-continued

Bacteriostatic Spectra

| | MIC (μM) | | | | |
| --- | --- | --- | --- | --- | --- |
| | Compound | | | | Control |
| Test microorganism: bacteria | 7-A | 7-B | 7-C | 7-D | comp'd[a] |
| Escherichia coli K12 W3110 | 0.9 | 0.9 | 0.45 | 0.2 | 25.6 |
| Bacillus subtilis IFO 3134 | 0.5 | 0.45 | 0.2 | 0.1 | 6.4 |
| Bacillus subtilis ATCC 6633 | 0.45 | 0.45 | 0.1 | 0.1 | 6.4 |
| Bacillus cereus IFO 3001 | 0.45 | 0.45 | 0.2 | 0.1 | 6.4 |
| Micrococcus luteus IFO 12708 | 0.2 | 0.2 | 0.1 | 0.1 | 6.4 |
| Staphylococcus aureus IFO 12732 | 0.45 | 0.45 | 0.2 | 0.1 | 6.4 |
| Staphylococcus aureus JCI (MRSA) | 0.4 | 0.45 | 0.45 | 0.2 | 12.8 |

[a]Benzalkonium: benzalkonium chloride

Test 2

Bactericidal Activities (MBC) of the Invention Compounds (7-A to 7-D) Against Various Bacteria As a control compound, benzalkonium bromide was used. Using five (5) Gram-negative bacteria and four (4) Gram-positive bacteria as test microorganisms, minimum bactericidal concentrations (MBCs) were determined in a similar manner as described above. The results are presented in Table 2.

TABLE 2

Bactericidal Spectra

| | MBC (μM)[a] | | | | |
| --- | --- | --- | --- | --- | --- |
| | Compound | | | | control |
| Test microorganism: bacteria | 7-A | 7-B | 7-C | 7-D | comp'd[b] |
| Pseudomonas aeruginosa ATCC 27583 | 3.6 | 3.6 | 0.9 | 0.45 | 204.8 |
| Klebsiella pneumoniae ATCC 13883 | 3.6 | 3.6 | 0.9 | 0.45 | 102.4 |
| Proteus rettgeri NIH 96 | 3.6 | 3.6 | 0.9 | 0.45 | 51.2 |
| Escherichia coli K12 OUT 8401 | 1.8 | 1.8 | 0.45 | 0.45 | 51.2 |
| Escherichia coli K12 W3110 | 1.8 | 1.8 | 0.45 | 0.45 | 204.8 |
| Bacillus subtilis IFO 3134 | 0.9 | 0.9 | 0.45 | 0.2 | 1.6 |
| Bacillus subtilis ATCC 6633 | 0.9 | 0.9 | 0.2 | 0.2 | 0.8 |
| Bacillus cereus IFO 3001 | 0.9 | 0.9 | 0.2 | 0.2 | 25.6 |
| Staphylococcus aureus IFO 12732 | 0.9 | 0.9 | 0.2 | 0.2 | 6.4 |

[a]MBC was determined by the dilution method. 30° C., 30 min.
[b]Benzalkonium: benzalkonium iodide Test 3

Determination of Minimum Inhibition Concentrations (MICs) of the Invention Compounds (7-A to 7-D) Against Eumycetes As a control compound, TBZ (2-(4'-thiozolyl)benzimidazole) was used. Each minimum inhibitory concentration (MIC) was determined as will be described hereinafter. Following the general broth dilution method, each test microorganisms which had been precultured with Sabouraud medium was diluted with humectant-added, sterilized water to prepare a spore suspension. Aliquots (1 mL) of diluted solutions of a compound were mixed with 1-mL aliquots of the spore suspension, respectively. After incubating the mixtures at 30° C. for 1 week in an incubator, turbidity was relied upon to determine whether or not any growth had taken place. The turbidity-free lowest concentration was recorded as MIC. The results are presented in Table 3.

TABLE 3

Antimold Spectra

| | MIC (μM)[a] | | | | |
| --- | --- | --- | --- | --- | --- |
| | Compound | | | | Control |
| Test microorganism: bacteria | 7-A | 7-B | 7-C | 7-D | comp'd |
| Aspergillus niger TSY 0013 | 3.6 | 3.6 | 1.8 | 0.9 | 102.4 |
| Aspergillus niger IFO 6341 | 3.6 | 3.6 | 1.8 | 0.9 | 25.6 |
| Aspergillus terreus IFO 6346 | 3.6 | 3.6 | 0.9 | 0.9 | 25.6 |
| Aureobasidium pullulans IFO 6353 | 3.6 | 3.6 | 1.8 | 0.9 | 0.8 |
| Chaetomium globosum IFO 6347 | 3.6 | 3.6 | 0.9 | 0.9 | 3.2 |
| Cladosporium cladosporioides IFO 6348 | 3.6 | 3.6 | 0.9 | 0.9 | 3.2 |
| Gliocladium virides IFO 6355 | 3.6 | 3.6 | 1.8 | 0.9 | 3.2 |
| Penicillium funiculosum IFO 6345 | 3.6 | 3.6 | 1.8 | 0.9 | 1.6 |
| Rhizopus nigricans SN 32 | 6.25 | 6.25 | 1.8 | 1.8 | 102.4< |
| Trichoderma virides IFO 30498 | 6.25 | 6.25 | 0.9 | 0.9 | 51.2 |

[a]MIC was determined by the broth dilution method while using Sabouraud medium. 30° C., 7 days.

INDUSTRIAL APPLICABILITY

According to the present invention, novel microbicidal pyridine compounds can be easily provided at low cost from readily-available pyridine compounds as starting raw materials.

The invention claimed is:

1. A microbicidal pyridine compound represented by the following formula (8) or formula (9):

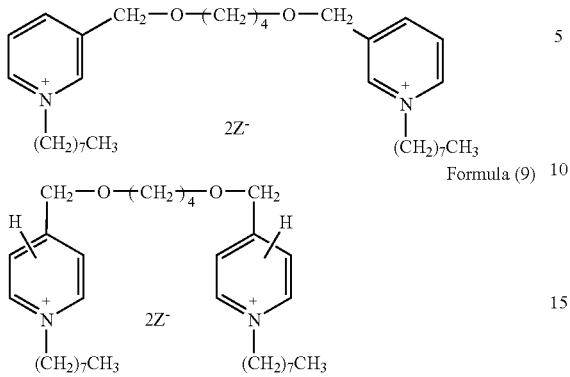

wherein Z is a chlorine atom, bromine atom or iodine atom or an $OSO_2R_1$ group in which $R_1$ is a lower alkyl group or a substituted or unsubstituted phenyl group.

2. A microbicidal pyridine compound represented by the following formula (10):

wherein R is a $-(CH_2)_9CH_3$ group or a $-(CH_2)_{11}CH_3$ group, Z is a chlorine atom, bromine atom or iodine atom or an $OSO_2R_1$ group in which $R_1$ is a lower alkyl group or a substituted or unsubstituted phenyl group.

* * * * *